US009368098B2

(12) United States Patent
Kappus et al.

(10) Patent No.: US 9,368,098 B2
(45) Date of Patent: Jun. 14, 2016

(54) PARAMETRIC EMITTER SYSTEM WITH NOISE CANCELATION

(71) Applicant: Turtle Beach Corporation, Poway, CA (US)

(72) Inventors: Brian Alan Kappus, San Diego, CA (US); Elwood Grant Norris, Poway, CA (US)

(73) Assignee: Turtle Beach Corporation, San Diego, CA (US)

( * ) Notice: Subject to any disclaimer, the term of this patent is extended or adjusted under 35 U.S.C. 154(b) by 0 days.

(21) Appl. No.: 14/511,517

(22) Filed: Oct. 10, 2014

(65) Prior Publication Data

US 2015/0104026 A1 Apr. 16, 2015

Related U.S. Application Data

(60) Provisional application No. 61/889,614, filed on Oct. 11, 2013.

(51) Int. Cl.

| | |
|---|---|
| ***A61F 11/06*** | (2006.01) |
| ***G10K 11/16*** | (2006.01) |
| ***H03B 29/00*** | (2006.01) |
| ***H04B 3/00*** | (2006.01) |
| ***H04B 15/00*** | (2006.01) |
| ***G10K 11/175*** | (2006.01) |
| ***G10K 15/08*** | (2006.01) |
| ***G10K 11/178*** | (2006.01) |
| ***H04R 1/10*** | (2006.01) |
| *H04R 3/00* | (2006.01) |

(52) U.S. Cl.

CPC ............ *G10K 11/175* (2013.01); *G10K 11/178* (2013.01); *G10K 15/08* (2013.01); *H04R 1/1083* (2013.01); *H04R 3/00* (2013.01); *H04R 2217/03* (2013.01)

(58) Field of Classification Search

CPC . G10K 11/175; G10K 15/08; G10K 11/1788; H04R 2217/03; H04R 3/00; H04R 1/1083

USPC ................................ 381/71.1, 71.2, 77, 94.7

See application file for complete search history.

(56) References Cited

U.S. PATENT DOCUMENTS

| | | | | |
|---|---|---|---|---|
| 4,829,590 | A * | 5/1989 | Ghose | G10K 11/178 381/71.8 |
| 6,151,397 | A * | 11/2000 | Jackson, Jr., II | G10L 21/0208 381/71.1 |
| 6,434,239 | B1 * | 8/2002 | DeLuca | G10K 11/1788 381/71.1 |
| 2003/0212328 | A1 | 11/2003 | Bechtold | |
| 2004/0234080 | A1 | 11/2004 | Hernandez | |

OTHER PUBLICATIONS

International Search Report and the Written Opinion for International App No. PCT/US2014/060173, mailed Mar. 16, 2015, Authorized Officer: Van Kerckhoven.

* cited by examiner

*Primary Examiner* — Vivian Chin

*Assistant Examiner* — Douglas Suthers

(74) *Attorney, Agent, or Firm* — Sheppard Mullin Richter & Hampton LLP

(57) ABSTRACT

An ultrasonic noise cancelation system can include a communication module configured to receive a noise signal detected by a noise detection module, the noise signal representing a noise sound in a listener environment; a noise cancelation module configured to invert the received noise signal thereby creating an inverse noise signal representing an inverse of the noise sound; and a modulator configured to modulate the inverse noise signal onto an ultrasonic carrier to generate an ultrasonic signal.

48 Claims, 7 Drawing Sheets

PARAMETRIC EMITTER SYSTEM WITH NOISE CANCELATION

CROSS-REFERENCE TO RELATED APPLICATIONS

This application claims the benefit of Provisional Patent Application Ser. No. 61/889,614, filed Oct. 11, 2013, and titled Ultrasonic Emitter System with Noise Cancelation, which is hereby incorporated by reference in its entirety.

TECHNICAL FIELD

The present disclosure relates generally to ultrasonic audio systems for a variety of applications. More particularly, some embodiments relate to systems and methods for active noise cancelation with an ultrasonic emitter system.

BACKGROUND OF THE INVENTION

Non-linear transduction results from the introduction of sufficiently intense, audio-modulated ultrasonic signals into an air column. Self-demodulation, or down-conversion, occurs along the air column resulting in the production of an audible acoustic signal. This process occurs because of the known physical principle that when two sound waves with different frequencies are radiated simultaneously in the same medium, a modulated waveform including the sum and difference of the two frequencies is produced by the non-linear (parametric) interaction of the two sound waves. When the two original sound waves are ultrasonic waves and the difference between them is selected to be an audio frequency, an audible sound can be generated by the parametric interaction.

Parametric audio reproduction systems produce sound through the heterodyning of two acoustic signals in a non-linear process that occurs in a medium such as air. The acoustic signals are typically in the ultrasound frequency range. The non-linearity of the medium results in acoustic signals produced by the medium that are the sum and difference of the acoustic signals. Thus, two ultrasound signals that are separated in frequency can result in a difference tone that is within the 60 Hz to 20,000 Hz range of human hearing.

SUMMARY

Embodiments of the technology described herein include systems and methods for performing noise cancelation in a listening environment. According to various embodiments, an ultrasonic audio system for canceling a noise sound from a listening environment includes an audio processing system in an ultrasonic emitter. The audio processing system can include, for example, a communication module configured to receive a noise signal detected by a noise detection module, the noise signal representing the noise sound in a listener environment; a noise cancelation module configured to invert the received noise signal thereby creating an inverse noise signal representing an inverse of the noise sound; and a modulator configured to modulate the inverse noise signal onto an ultrasonic carrier to generate an ultrasonic signal.

An example ultrasonic emitter can be coupled to receive the ultrasonic signal and configured to launch an ultrasonic pressure wave representing the ultrasonic signal into a transmission medium in the listening environment, wherein upon transmission in the transmission medium, the ultrasonic signal demodulates, thereby producing an inverse of the noise sound in the listening environment.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the accompanying figures. The drawings are provided for purposes of illustration only and merely depict typical or example embodiments of the invention. These drawings are provided to facilitate the reader's understanding of the systems and methods described herein, and shall not be considered limiting of the breadth, scope, or applicability of the claimed invention.

Some of the figures included herein illustrate various embodiments of the invention from different viewing angles. Although the accompanying descriptive text may refer to elements depicted therein as being on the "top," "bottom" or "side" of an apparatus, such references are merely descriptive and do not imply or require that the invention be implemented or used in a particular spatial orientation unless explicitly stated otherwise.

The figures are not intended to be exhaustive or to limit the invention to the precise form disclosed. It should be understood that the invention can be practiced with modification and alteration, and that the invention be limited only by the claims and the equivalents thereof.

DESCRIPTION

Embodiments of the systems and methods described herein provide a HyperSonic Sound (HSS) audio system or other ultrasonic audio system for a variety of different applications. Particularly, in some embodiments, ultrasonic emitter systems can be configured to include noise cancelation to cancel (e.g., reduce or completely canceled) a noise sound in a listening environment. The noise sound can include, for example, one or more background sounds or noises, unwanted sounds or noises, and other sounds or noises generated in or reaching the listening environment that are different from audio content intended for listener or that is listener may otherwise not wish to hear.

Figure 1:
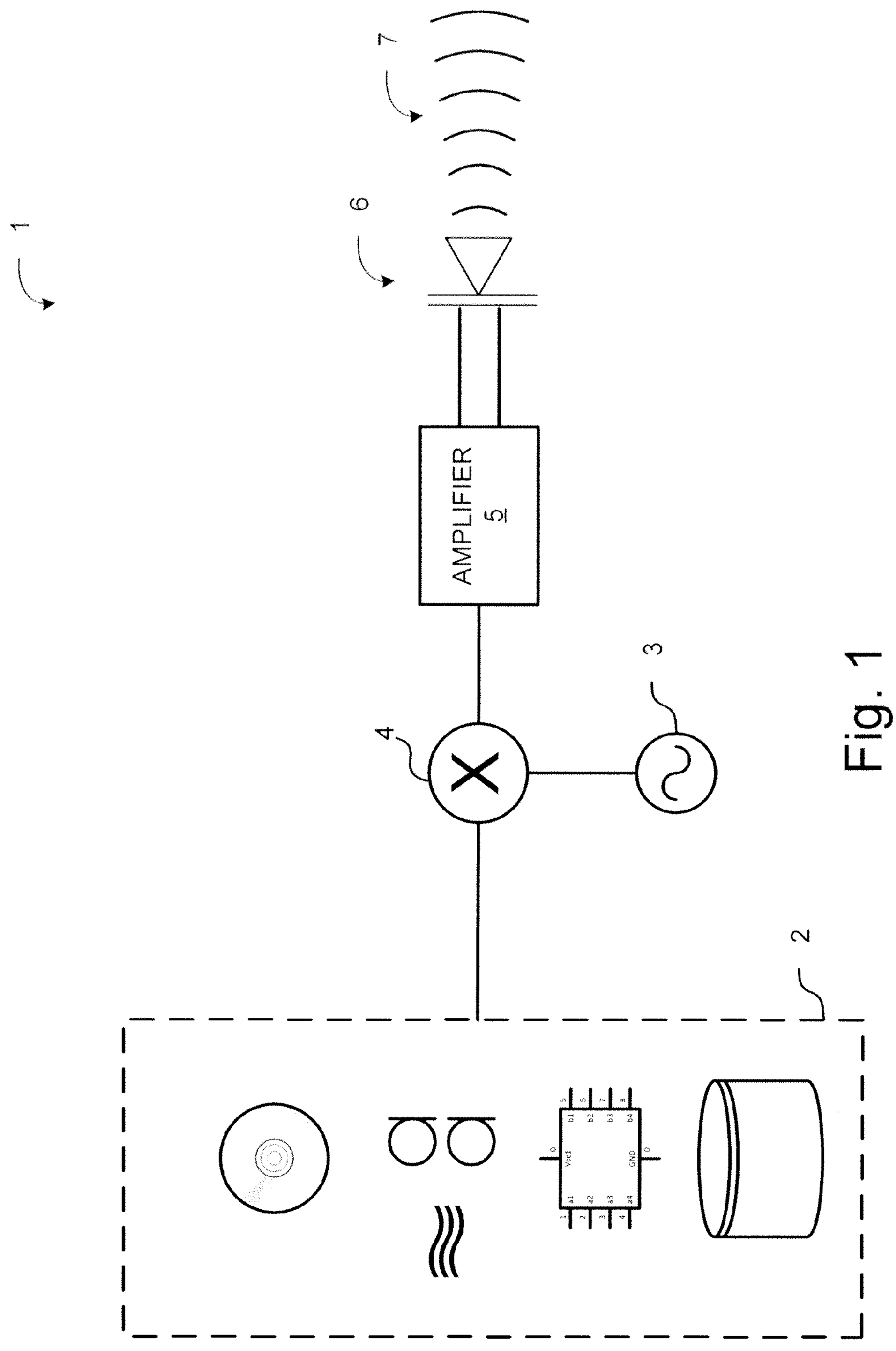
FIG. 1 is a diagram illustrating an ultrasonic sound system suitable for use with the emitter technology described herein.

Before describing systems and methods for noise cancelation in detail, it is useful to describe an example ultrasonic audio system with which noise cancelation may be implemented. FIG. 1 is a diagram illustrating an ultrasonic sound system suitable for use in conjunction with the systems and methods described herein. In this exemplary ultrasonic audio system 1, audio content from an audio source 2, such as, for example, a microphone, memory, a data storage device, streaming media source, MP3, CD, DVD, set-top-box, or other audio source is received. The audio content may be decoded and converted from digital to analog form, depending on the source. The audio content received by the exemplary ultrasonic audio system 1 is modulated onto an ultrasonic carrier of frequency f1, using a modulator. The modulator typically includes a local oscillator 3 to generate the ultrasonic carrier signal, and multiplier 4 to modulate the audio signal on the carrier signal. The resultant signal is a double- or single-sideband signal with a carrier at frequency f1 and one or more side lobes. In some embodiments, the signal is a parametric ultrasonic wave or a HSS signal. In most cases, the modulation scheme used is amplitude modulation, or AM, although other modulation schemes can be used as well. Amplitude modulation can be achieved by multiplying the ultrasonic carrier by the information-carrying signal, which in this case is the audio signal. The spectrum of the modulated signal can have two sidebands, an upper and a lower side band, which are symmetric with respect to the carrier frequency, and the carrier itself.

The modulated ultrasonic signal is provided to the ultrasonic transducer 6, which launches the ultrasonic signal into the air creating ultrasonic wave 7. When played back through the transducer at a sufficiently high sound pressure level, due to nonlinear behavior of the air through which it is 'played' or transmitted, the carrier in the signal mixes with the sideband(s) to demodulate the signal and reproduce the audio content. This is sometimes referred to as self-demodulation. Thus, even for single-sideband implementations, the carrier is included with the launched signal so that self-demodulation can take place.

Although the system illustrated in FIG. 1 uses a single transducer to launch a single channel of audio content, one of ordinary skill in the art after reading this description will understand how multiple mixers, amplifiers and transducers can be used to transmit multiple channels of audio using ultrasonic carriers. The ultrasonic transducers can be mounted in any desired location depending on the application.

Any of a number of transducer types can be used with the ultrasonic audio system including, for example, electrostatic, piezoelectric, and other ultrasonic transducers. Examples of ultrasonic transducers that can be used with the systems and methods described herein are described in U.S. Pat. No. 8,718,297, titled Parametric Transducer and Related Methods, which is Incorporated by reference herein in its entirety as if reproduced in full below. Transducers such as, for example, ultrasonic transducer 6 are also referred to herein as emitters, or ultrasonic emitters.

Figure 2:
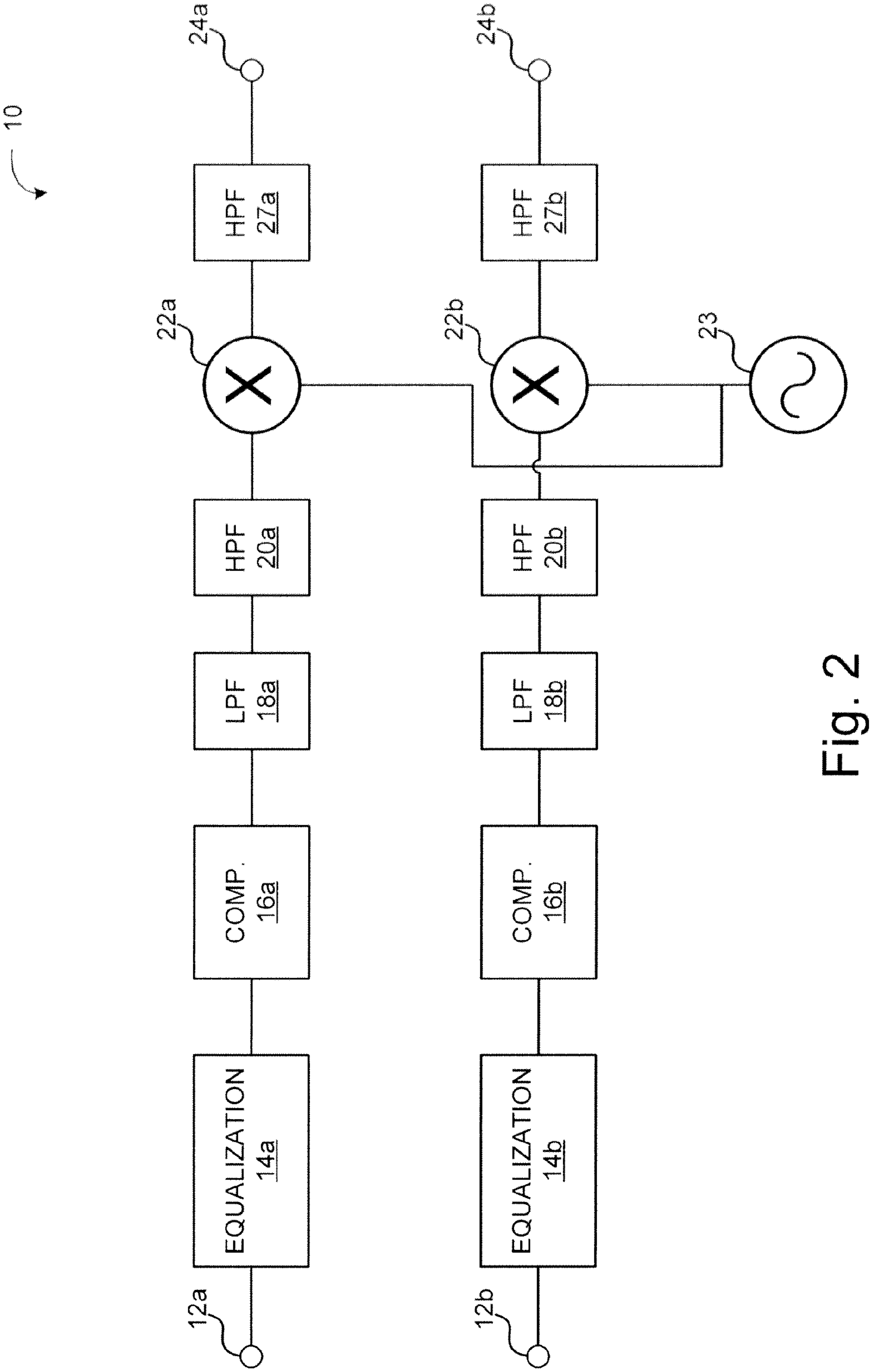
FIG. 2 is a diagram illustrating another example of a signal processing system that is suitable for use with the emitter technology described herein.

One example of a signal processing system 10 that is suitable for use with the technology described herein is illustrated schematically in FIG. 2. In this embodiment, various processing circuits or components are illustrated in the order (relative to the processing path of the signal) in which they are arranged according to one implementation. It is to be understood that the components of the processing circuit can vary, as can the order in which the input signal is processed by each circuit or component. Also, depending upon the embodiment, the signal processing system 10 can include more or fewer components or circuits than those shown.

Also, the example shown in FIG. 1 is optimized for use in processing two input and output channels (e.g., a "stereo" signal), with various components or circuits including substantially matching components for each channel of the signal. It will be understood by one of ordinary skill in the art after reading this description that the audio system can be implemented using a single channel (e.g., a "monaural" or "mono" signal), two channels (as illustrated in FIG. 2), or a greater number of channels.

Referring now to FIG. 2, the example signal processing system 10 can include audio inputs that can correspond to left 12*a* and right 12*b* channels of an audio input signal. Equalizing networks 14*a*, 14*b* can be included to provide equalization of the signal. The equalization networks can, for example, boost or suppress predetermined frequencies or frequency ranges to increase the benefit provided naturally by the emitter/inductor combination of the parametric emitter assembly.

After the audio signals are equalized, compressor circuits 16*a*, 16*b* can be included to compress the dynamic range of the incoming signal, effectively raising the amplitude of certain portions of the incoming signals and lowering the amplitude of certain other portions of the incoming signals. More particularly, compressor circuits 16*a*, 16*b* can be included to narrow the range of audio amplitudes. In one aspect, the compressors lessen the peak-to-peak amplitude of the input signals by a ratio of not less than about 2:1. Adjusting the input signals to a narrower range of amplitude can be done to minimize distortion, which is characteristic of the limited dynamic range of this class of modulation systems. In other embodiments, the equalizing networks 14*a*, 14*b* can be provided after compressor circuits 16*a*, 16*b*, to equalize the signals after compression.

Low pass filter circuits 18*a*, 18*b* can be included to provide a cutoff of high portions of the signal, and high pass filter circuits 20*a*, 20*b* providing a cutoff of low portions of the audio signals. In one exemplary embodiment, low pass filter circuits 18*a*, 18*b* are used to cut signals higher than about 15-20 kHz, and high pass filter circuits 20*a*, 20*b* are used to cut signals lower than about 20-200 Hz.

The low pass filter circuits 18*a*, 18*b* can be configured to eliminate higher frequencies that, after modulation, could result in the creation of an audible beat signal with the carrier. By way of example, if a low pass filter cuts frequencies above 15 kHz, and the carrier frequency is approximately 44 kHz, the difference signal will not be lower than around 29 kHz, which is still outside of the audible range for humans. However, if frequencies as high as 25 kHz were allowed to pass the filter circuit, the difference signal generated could be in the range of 19 kHz, which is within the range of human hearing.

Figure 6:
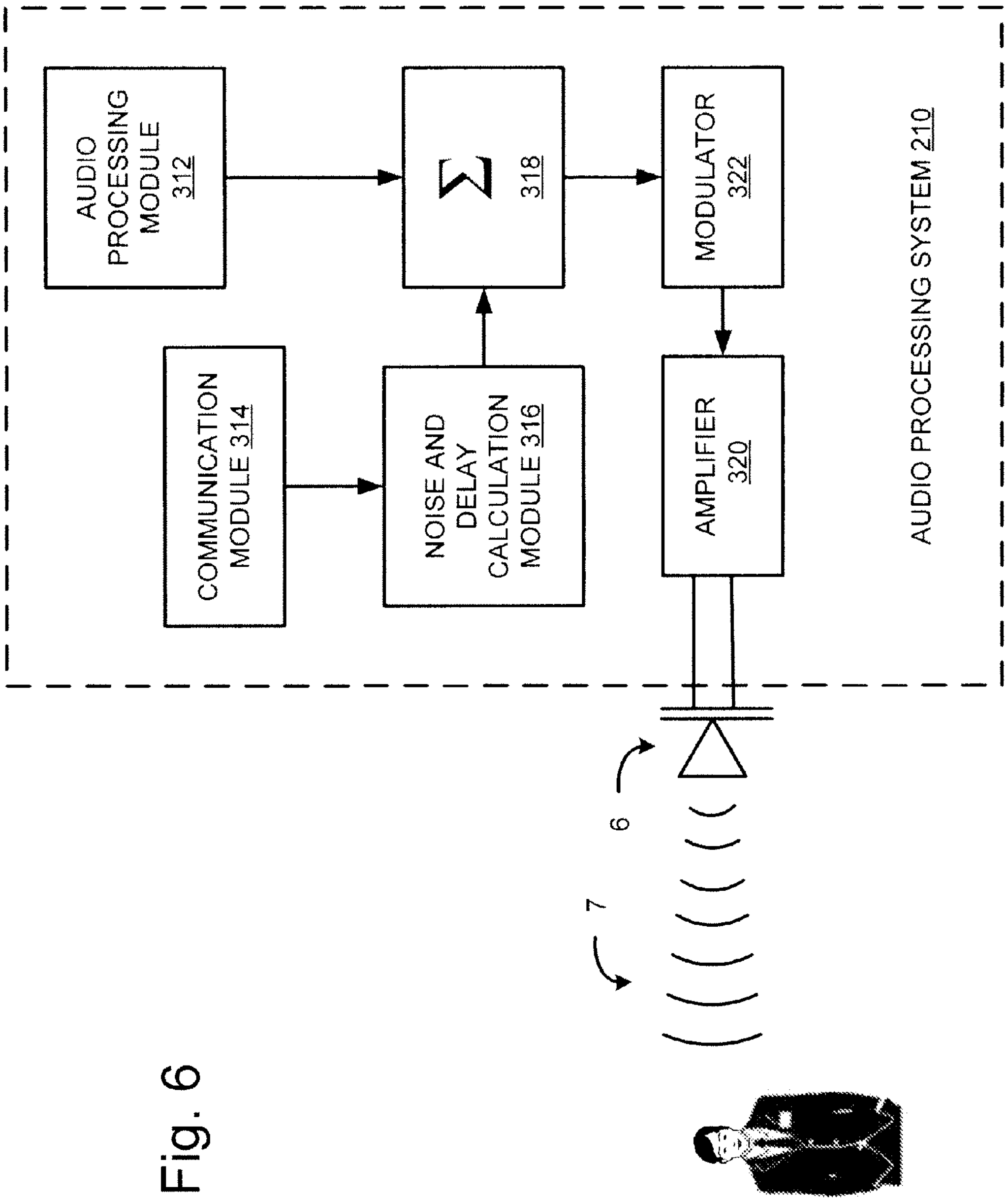
FIG. 6 is a diagram illustrating another example of an audio processing system 210 that can be used in a noise canceling ultrasonic emitter system.

The high pass filter circuits 20*a*, 20*b* can be configured to eliminate low frequencies that, after modulation, would result in deviation of carrier frequency (e.g., those portions of the modulated signal of FIG. 6 that are closest to the carrier frequency). Also, some low frequencies are difficult for the system to reproduce efficiently and as a result, much energy can be wasted trying to reproduce these frequencies. Therefore, high pass filter circuits 20*a*, 20*b* can be configured to cut out these frequencies.

In the example signal processing system 10, after passing through the low pass and high pass filters, the audio signals are modulated by modulators 22*a*, 22*b*. Modulators 22*a*, 22*b*, mix or combine the audio signals with a carrier signal generated by oscillator 23. For example, in some embodiments a single oscillator is used to drive both modulators 22*a*, 22*b*. By utilizing a single oscillator for multiple modulators, an identical carrier frequency is provided to multiple channels being output at 24*a*, 24*b* from the modulators. Using the same carrier frequency for each channel lessens the risk that any audible beat frequencies may occur. It is noted that in digital implementations, the use of crystal oscillators can be avoided.

While compression, equalization and filtering are useful for reproducing desired audio content (e.g., music, voice, etc.), applying these processes to noise cancelation signals may interfere with the effectiveness of such noise cancelation signals. In other words, it is desirable to reproduce the noise so that it matches the actual noise as closely as possible. Therefore, aside from the application of transfer functions (discussed in detail below), compression, equalization and filtering can be omitted for the noise signal so that the inverted noise produced at the listener can more effectively cancel the actual noise reaching the listener. Accordingly, in various embodiments, compression, equalization and filtering may be used for the audio content generated by the ultrasonic audio system, and may bypassed for the noise cancelation signals. Furthermore, in some embodiments, equalization may be applied differently to the noise signals as part of the transfer function (again, discussed below). Accordingly, systems can be implemented in which the audio path is different from the noise cancelation path and the signals can be combined before modulation.

High-pass filters 27*a*, 27*b* can also be included after the modulation stage. High-pass filters 27*a*, 27*b* can be used to pass the modulated ultrasonic carrier signal and ensure that no audio frequencies enter the amplifier via outputs 24*a*, 24*b*. Accordingly, in some embodiments, high-pass filters 27*a*, 27*b* can be configured to filter out signals below about 25 kHz.

According to various embodiments of the systems and methods described herein, ultrasonic emitter systems can be configured to include noise cancelation to cancel a noise sound from a listening environment. The noise sound can include, for example, one or more background sounds or noises, unwanted sounds or noises, and other sounds or noises generated in or reaching the listening environment that are different from audio content intended for listener or that is listener may otherwise not wish to hear.

The cancelation can include reducing or completely canceling out a noise sound from a listening environment. In accordance with various embodiments, a listener in a listening environment can enjoy the listening environment with some or all of the noise sound in the environment eliminated or reduced at the listener. This can be accomplished while the listener is listening to audio content delivered by the ultrasonic emitter system. In further embodiments, this can be accomplished even while the listener is not listening to audio content via the emitter system simply by delivering an ultrasonic carrier to the listener with the appropriate noise cancelation signals (examples of which are described below).

In some embodiments, a noise detection module can be provided in the listening environment to detect a noise sound. The detected noise sound can be captured and provided to a noise cancelation module of the ultrasonic emitter system. The ultrasonic emitter system creates an inverse of the noise sound, adds this inverted noise to the audio content (with delay and processing transfer functions in some embodiments) and modulates the combined content onto an ultrasonic carrier for delivery by the ultrasonic emitter. Upon reaching the listener, the inverted noise component of the combined signal cancels the noise sound (completely or partially) leaving behind the demodulated audio content (in embodiments in which audio content is included) to be enjoyed by the listener.

In situations where the listener is not listening to audio content, the ultrasonic emitter system can still be used to reduce or even eliminate the noise sound. For example, similar techniques can be used to capture the noise sound, invert it (with delay and processing transfer functions in some embodiments), and modulate it onto the ultrasonic carrier. The ultrasonic signal demodulates in the air on the way to the listener, reproducing an inverse of the noise sound. This inverse of the noise sound combines with the noise sound itself to reduce or eliminate (i.e., cancel) the noise sound as heard by the intended listener (one or more persons in the listening environment). In various embodiments, multiple emitters can be used to direct noise cancelation signals to multiple different locations in the listening environment.

Figure 3:
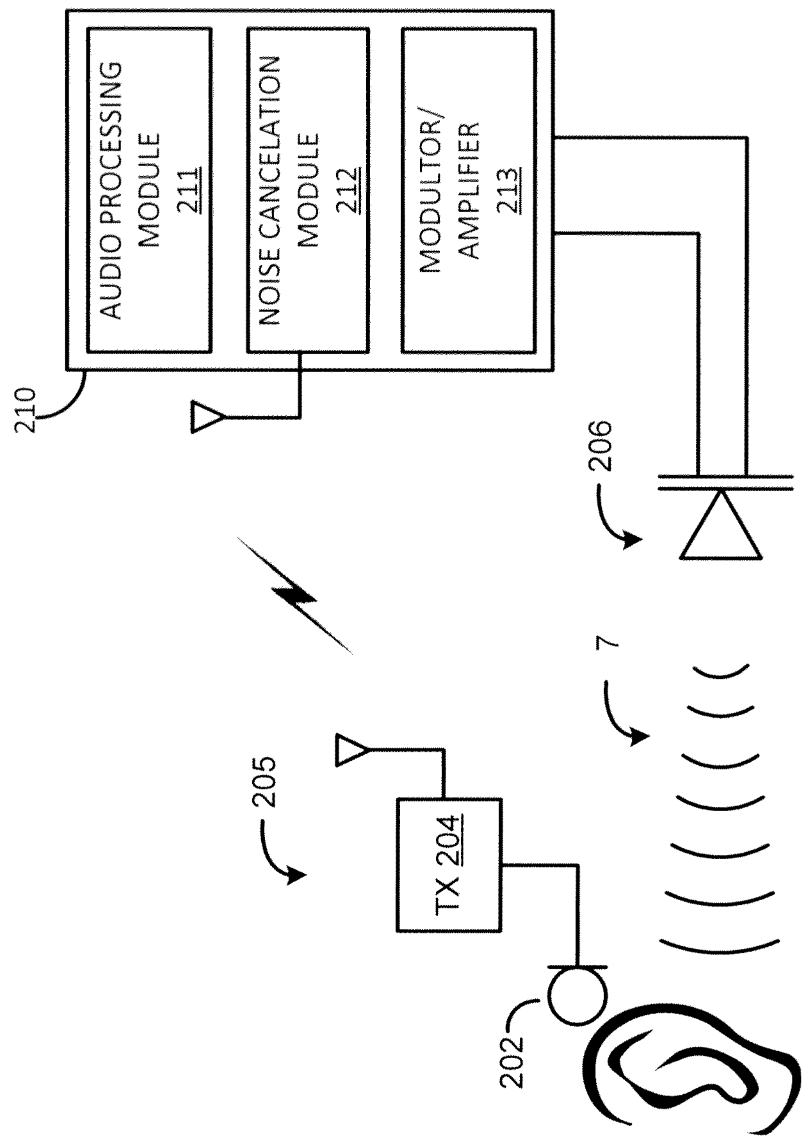
FIG. 3 is a diagram illustrating an example of noise cancelation in an ultrasonic emitter system in accordance with one embodiment of the systems and methods described herein.

Having thus generally described systems and techniques for noise cancelation, a few example embodiments are now described. FIG. 3 is a diagram illustrating an example of noise cancelation in an ultrasonic emitter system in accordance with one embodiment of the systems and methods described herein. Referring now to FIG. 3, in this example the ultrasonic emitter system includes an audio processing system 210, an ultrasonic emitter 206, and a noise detection module 205.

In the illustrated example, audio processing system 210 includes an audio processing module 211, a noise cancelation module 212, and a modulation/amplification module 213. Audio processing system 210 can be configured to receive audio content to be delivered to the listener, process the audio content such as, for example, using equalization and compression, filtering and so on. For example, in one embodiment, audio processing module 211 can be implemented to include the equalization, compression, low pass filtering, and high pass filtering components (14-20) as shown in FIG. 2. After reading this description, one of ordinary skill in the art will understand how these or other components can be used in an audio processing module 211. In some embodiments, the modulation of the audio signal onto an ultrasonic carrier can be performed by audio processing module 211 as can additional high pass filtering and processing. In other embodiments, modulation onto an ultrasonic carrier can take place after the audio content is combined with the noise cancelation signal (described below).

Noise cancelation module 212 can be configured to receive noise content from one or more noise detection modules 205. Noise cancelation module can include the appropriate communications interfaces, whether wired or wireless, to receive a signal representative of the noise. The communications interface can be further configured to demodulate the noise and provide a noise signal for processing. Noise cancelation module 212 can further be configured to convert the noise signal.

Audio processing system 210 can be configured to combine the audio content with the inverted noise signal to create a combined signal. The combined signal can be modulated onto an ultrasonic carrier, and the audio-modulated ultrasonic signal amplified for delivery to ultrasonic emitter 206. The modulation and amplification can be performed by modulation/amplification module 213. An example of modulating audio content onto an ultrasonic carrier is provided at FIG. 2 in which mixers 22 mix a carrier signal (for example, one generated by the oscillator 23 (e.g., a local oscillator)) with the audio content to modulate the content onto the carrier. Although amplification is not shown in FIG. 2, an example of an amplifier stage 5 after the modulation stage is illustrated at FIG. 1.

The modulated combined audio/inverted-noise signal is provided to an ultrasonic emitter 206. Ultrasonic emitter 206 can be implemented using any of a number of different ultrasonic emitters including electrostatic, piezoelectric, or other emitters. In operation, the ultrasonic signal 207 travels to the listener and demodulates in the medium between the ultrasonic emitter 206 and the listener (e.g., in the air). At the listener, the demodulated audio/inverted-noise content combines with the noise sound as detected by noise detection module 205. The inverted-noise sound cancels, partially or completely, the noise sound at the listener.

Noise detection module 205 can comprise any of a number of instrumentalities to detect noise sound and send the noise sound to audio processing system 210. In the example illustrated in FIG. 3, noise detection module 205 includes a microphone 202, and a transmitter 204. Microphone 202 is used to detect the noise sound and convert the noise sound to an electrical signal representing the noise sound. Transmitter 204 can be configured to include an amplifier to amplify the signal and a transmitter to transmit the signal to audio processing system 210 via a wired or wireless communication link. As shown in the example, an antenna can be provided for wireless communications. Any of a number of standardized communications protocols can be used as can a variety of different proprietary communication protocols. Amplification can also be provided at a transmitter to amplify the signals prior to transmission. In other embodiments, noise detection module 205 can simply be a microphone 202 configured to be plugged directly into mic inputs at the audio processing system 210.

In the example illustrated in FIG. 3, microphone 202 is positioned proximal to the listener to detect noise as it reaches the listener. In application, one or more microphones can be positioned on the listener to pick up the noise sound as it reaches the listener. For example, in some embodiments, a microphone can be worn behind the listener's ear, on the listener's lapel, on a clip mounted to glasses worn by the listener and so on. As these examples serve to illustrate, there are number of locations on or near the listener at which one or more microphones can be mounted. Similarly, transmitter 204 can be configured to be worn by or placed in the pocket of the listener. Wired or wireless microphones can be used to present a wired or wireless interface between the microphones and the transmitter. Ideally, noise detection module 205 is self-powered using battery power, solar power, or other unwired power sources, although wired powered sources can also be used.

In embodiments where a microphone of a noise detection module 205 is positioned proximal to the listener, the system may be well-suited to cancel or diminish the effects of a steady-state noise sound. Where the sound is relatively steady-state, constant, or unchanging, it is possible to use system such as those described herein to detect the noise as it reaches the ear of the listener and provide an appropriate noise cancelation system to cancel it out fully or partially. For time varying noise signals, the system must be configured to transmit a signal representing the detected noise sound to the processing system, invert the noise sound, combine it with the audio content, and deliver it to the user via the ultrasonic carrier quickly enough so that the inverted noise sound corresponds to the actual noise sound reaching the listener's ear (e.g. they are out of phase so that cancelation takes place). Depending on the distances between the listener and the ultrasonic system, it may be impossible to process time varying noises quickly enough due to the time it takes for the noise signal to reach the ultrasonic emitter system, the processing time required, and the time it takes for the audio-modulated ultrasonic signal to reach the listener. In some embodiments, however, where the microphone 202 can be placed closer to the noise source and physically separate from the listener, the ability to cancel time varying noises may be provided. Examples of this are discussed in further detail below with reference to FIG. 4.

In further embodiments, whether using proximal (to the listener) or remote microphones, the audio processing system 210 can be implemented to cancel time varying content where the time varying content is known. For example, consider a scenario where a listener is listening to an audio program delivered by a media device such as, for example, a television, a radio, a stereo, or other audio sound generator. Further consider in this scenario that the listener has a companion that does not want to hear the audio content that the listener is enjoying. For example, the companion may be sleeping, studying, or otherwise engaged in activity and does not want to be disturbed by the audio content. In this scenario, the audio program is a noise sound for the listener's companion. In some embodiments, the system can be configured such that the audio program can be fed to the ultrasonic noise cancelation system, inverted by the noise cancelation system, and the inverted audio program (i.e. inverted noise) delivered to the companion by any ultrasonic emitter. The signal demodulates in the air on the way to the companion and cancels out the "noise" from the media device. Because of the directional nature of ultrasonic signals, the inverted noise can be delivered directly to the companion.

Because the cancelation will not be ideal where the inverted content reaches the listener at a time delayed relative to the actual content, a delay mechanism can be built into the media player to accommodate this. For example, the audio program from the media player can be fed to the ultrasonic noise cancelation system and, rather than fed directly for playback can be buffered or otherwise delayed. In the corresponding video or other content can also be delayed to maintain the original integrity of the overall content package. The amount of delay can be calculated based on the distance distances between and among the media player, the companion, and the ultrasonic noise cancelation system. Particularly, the amount of delay can be calculated such that the combined inverse noise and audio content delivered by the media player reaches the companion at the same time or substantially the same time as the actual noise sound reaches the companion such that noise sound cancelation occurs. In one embodiment, an amount of delay is injected such that the inverse noise sound reaching the listener from the ultrasonic emitter is the inverse of (e.g., 180° out of phase) or substantially the inverse of the noise sound reaching the listener from the actual noise source.

In yet another embodiment, the system can be configured such that the emitter of the ultrasonic noise cancelation system is positioned nearby to the audio speaker of the media device such that audio content from the media device can be captured directly (e.g., via line out plugs from the media device, hardwiring into the media device, positioning a microphone adjacent the speaker of the media device, and so on) and can be delivered to the adjacent ultrasonic noise cancelation system. This eliminates or substantially reduces the latency otherwise associated with delivering the audio content to be canceled from the media device to the ultrasonic noise cancelation system. However, because there still may be some delay in the system (due to processing and modulation of the noise signal, etc.), the noise cancelation signal may arrive too late to be 180° (or substantially close thereto) out of phase with the noise.

In still further embodiments, the ultrasonic emitters of the noise cancelation system can be integrated into headphones or earpieces, as can audio processing system 210.

Figure 4:
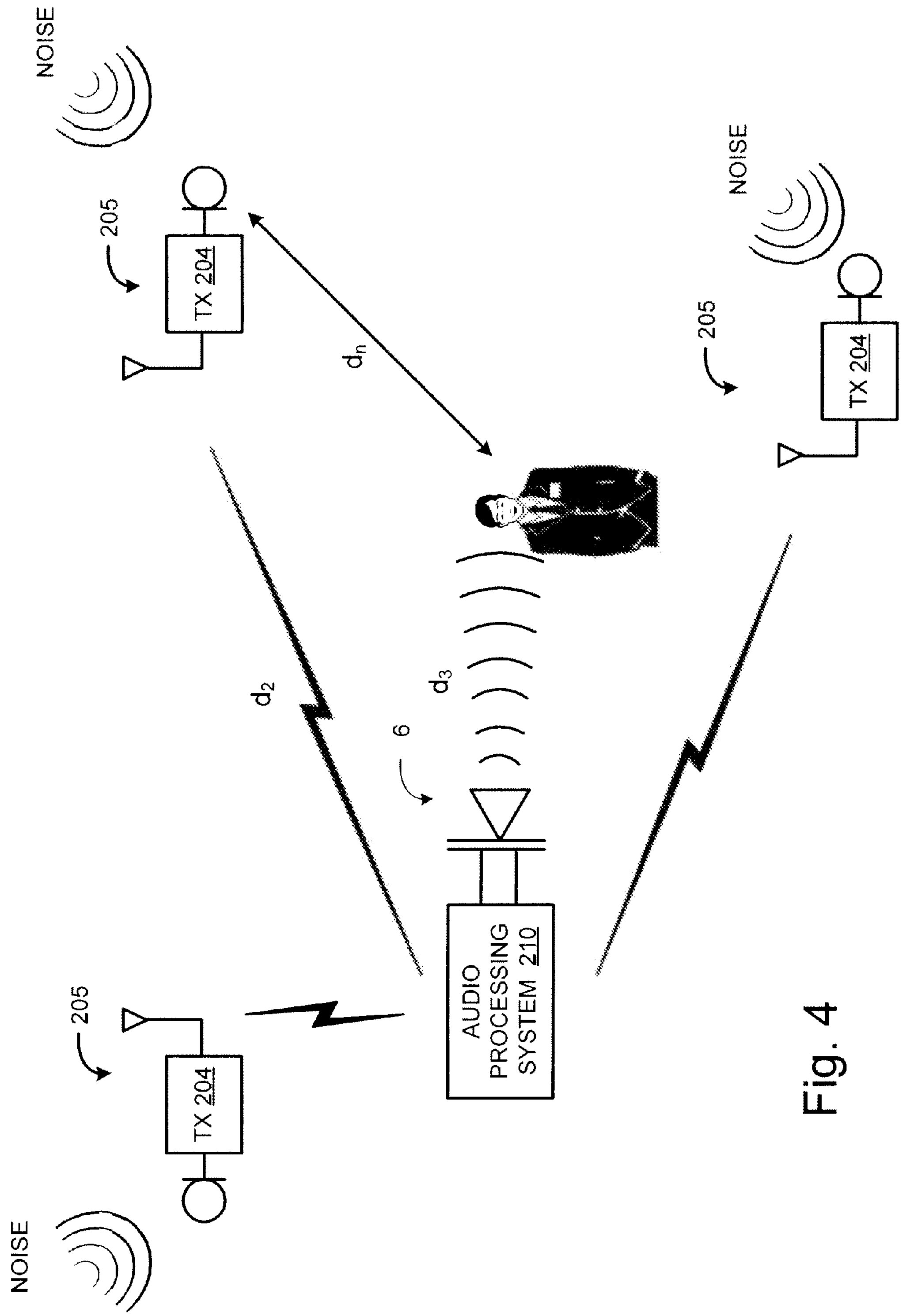
FIG. 4 is a diagram illustrating an example ultrasonic noise cancelation system using a plurality of remote noise detection modules in accordance with various embodiments of the technology disclosed herein.

As noted above, one example configuration that can be used to provide cancelation for time varying sounds is to provide one or more microphones at a distance from the listener to detect a noise sound. Preferably, the microphones are placed at a sufficient distance from the listener such that the noise cancelation system has sufficient time to generate, delay and deliver the cancelation signal can to the listener so that it reaches the listener at the same time as the actual noise sound. An example of this is provided in FIG. 4. Particularly, FIG. 4 is a diagram illustrating an example ultrasonic noise cancelation system using a plurality of remote noise detection modules in accordance with various embodiments of the technology disclosed herein. The microphone or noise detection module that is remote to the listener is one that is far enough away from the listener such that an inverse of the noise sound detected by the noise detection module can be created and delivered by the audio processing system and ultrasonic emitter to the listener (with or without inserted delay) such that the inverted noise sound reaches the listener in time to cancel the actual noise sound.

Referring now to FIG. 4, this particular example includes three noise detection modules 205 located at some distance remote from the listener. Preferably, each noise detection module 205 is configured to detect incoming noise at a time $T_0$ before it reaches the listener at a later time. Although not shown in the example of FIG. 4, one or more noise detection systems can also be provided proximal to the listener (e.g. similar to that as shown in FIG. 3). In various embodiments, a noise detection module located proximal to the listener can, for example, be a noise detection module with a microphone (or other noise sound reception device) located at or near the listener's ears. For example, a noise detection module proximal the listener can include a microphone worn by the listener at or near his or her head, behind the ear, on the lapel, or otherwise close to the listener.

Although not illustrated in FIG. 4, in this and other embodiments, a feedback microphone can be positioned at the listener to provide feedback to the system on system performance, or to be used to characterize the system (examples of which are described below), or both. In a feedback mode, the system can be configured to use the feedback microphone to pick up audio at the listener (including any remaining noise) and provide a signal representing this audio to the cancelation system. The cancelation system can be configured to evaluate the actual noise levels reaching the listener with the noise cancelation in operation to verify the effectiveness of the noise cancelation. In some embodiments, the noise cancelation can be switched on and off during the feedback process to measure the effectiveness. In further embodiments, the noise cancelation transfer function(s) (described below) can be adjusted (e.g., in real time) and the effects of such adjustment measured using feedback provided by the microphone at the listener, to optimize the transfer function(s) for improved noise cancelation. In various embodiments, the feedback microphone can be a dedicated feedback microphone, or the feedback functions can be shared with a microphone of a noise detection module located at the listener location.

The noise detection modules 205 shown in FIG. 4 can be configured to detect the noise sound, and send the noise sound to audio processing system 210 for inversion, processing and delivery to the listener. The example of FIG. 4 also includes an audio processing system 210 that can be configured to receive a signal representing the noise sound, create an inverse representation of the noise, combine the inverse noise with the audio content, modulate the combined audio content and inverse-noise content onto an ultrasonic carrier and deliver the ultrasonic signal to the emitter.

In some embodiments, the noise signals can be processed without audio content. In this case, the inverse noise signal is modulated onto the carrier without being combined with any audio content. In this case a noise cancelation signal only, without any other audio content (such as, for example, program content) is delivered to the listener via the ultrasonic transmission. In such embodiments, the system can have the effect of reducing background or other noise sound in an environment even though it is not delivering audio content from an audio source (such as, for example, an audio source 2 as shown in FIG. 1).

In some embodiments, the microphones included at the noise detection modules 205 can be directional microphones such that the time it takes for a noise from the noise source at a given location to reach the listener can be calculated. Preferably, directional microphones are configured to detect noise sources linearly aligned with a line between the listener and the microphone. In such configurations, and given a known distance between the microphone and the listener, the time of travel of the noise from the microphone to the listener can be accurately determined. Accordingly, the system can be configured in an environment such that directional microphones are positioned between sources of the noise sounds of interest (i.e. noise sources that one wishes to cancel) and the listener.

Where microphones are implemented having a wide field of reception, other noises coming from other directions (including potentially from the other side of the listener) can potentially be detected by the microphone inverted by the system and provided to the listener which can add noise sound into the environment. Accordingly, the directionality of the microphones can be selected to detect noise sounds such that their time of arrival at the listener is predictable, or sufficiently predictable such that the delay can be calculated sufficiently well to provide a suitable inverse noise sound to the listener. Where there are multiple noise sources positioned at different locations throughout the environment, multiple microphones (and multiple noise detection systems) can be included to detect those noises on their way to the listener.

The ultrasonic noise cancelation system can be configured to determine a time at which the actual noise sound is predicted to reach the listener and to introduce the appropriate amount of delay into the inverted noise signal such that the inverted noise sound reaches the listener at the same, substantially the same, or approximately the same time as the corresponding actual noise sound (e.g, they are exactly, substantially or approximately 180° out of phase with one another). Accordingly, in various embodiments, the system can be configured to know the distances between and among the various components in the system and the listener, and use those distances to determine an amount of delay time to interject.

An example of this is described with reference to FIG. 4. In particular, an example of this is described with reference to the noise detection module 205 in the upper right-hand corner of FIG. 4. In this example, the system can be configured to determine the distance $d_n$ between the microphone and the listener, the distance $d_2$ between the antenna of noise detection module 205 and the antenna of audio processing system 210, and the distance $d_3$ between emitter 6 and the listener. Additionally, internal delays can be determined and used in the calculation to provide a better estimate of the amount of delay required such that the inverse of the noise sound reaches the listener at the same time as the corresponding noise reaches the listener. These internal delays can include internal delays $d_4$ of the noise detection module 205 and internal delays $d_5$ of the audio processing system 210. Internal delays of the noise detection module 205 $d_4$ can include the delay from the time the noise is detected by the microphone until such time as a signal representing the noise is transmitted by the antenna. Internal delays of the audio processing system 210 $d_5$ can include the delay from the time the signal representing the noise sound is received at the audio processing system 210 until the signal representing the inverse of the noise sound is emitted by ultrasonic transducer 6.

Accordingly, the system can be configured to inject an additional amount of delay, dx, into the system such that:

$$dn=d2+d3+d4+d5+dx \quad (1.1)$$

As this illustrates, where the microphone is close enough to the listener such that dn<d2+d3+d4+d5, it may be impossible, without other changes, to cause the inverted audio signal to reach the listener at the same time as the corresponding actual noise. Changes such as relocating the microphone to increase dn, or selecting components to decrease the internal delays can help to avoid or resolve this situation.

As the above illustrates, in order to increase or maximize the amount of cancelation provided by the system, it is useful to know the distances between and among the components and the listener. Where the listener is in a fixed listening position and the components are fixed, this can be a trivial task. However, in situations where the listener or the components or all of the above are subject to movement or relocation relative to one another the system can be configured to calculate the distances and determine the delay that needs to be introduced into the inverted noise in real time. Accordingly, a variety of position location systems and techniques can be used to determine the position of the components relative to one another as well as the position of the components relative to the listener. For example, two-dimensional or three-dimensional position sensors can be included to detect the position of the listener in listening area. Optical, infrared, RF, ultrasonic, sonic, or other type of position sensors can be used to determine the location of the listener in the listening area. Additionally, GPS, cellular or other triangulation techniques can be used to determine the position of the listener. Similar techniques can also be used to determine the position of the various components in the system. Once the positions of the listener and the components are determined, the delay can be calculated based on the distances between the various objects and the internal delays.

Figure 5:
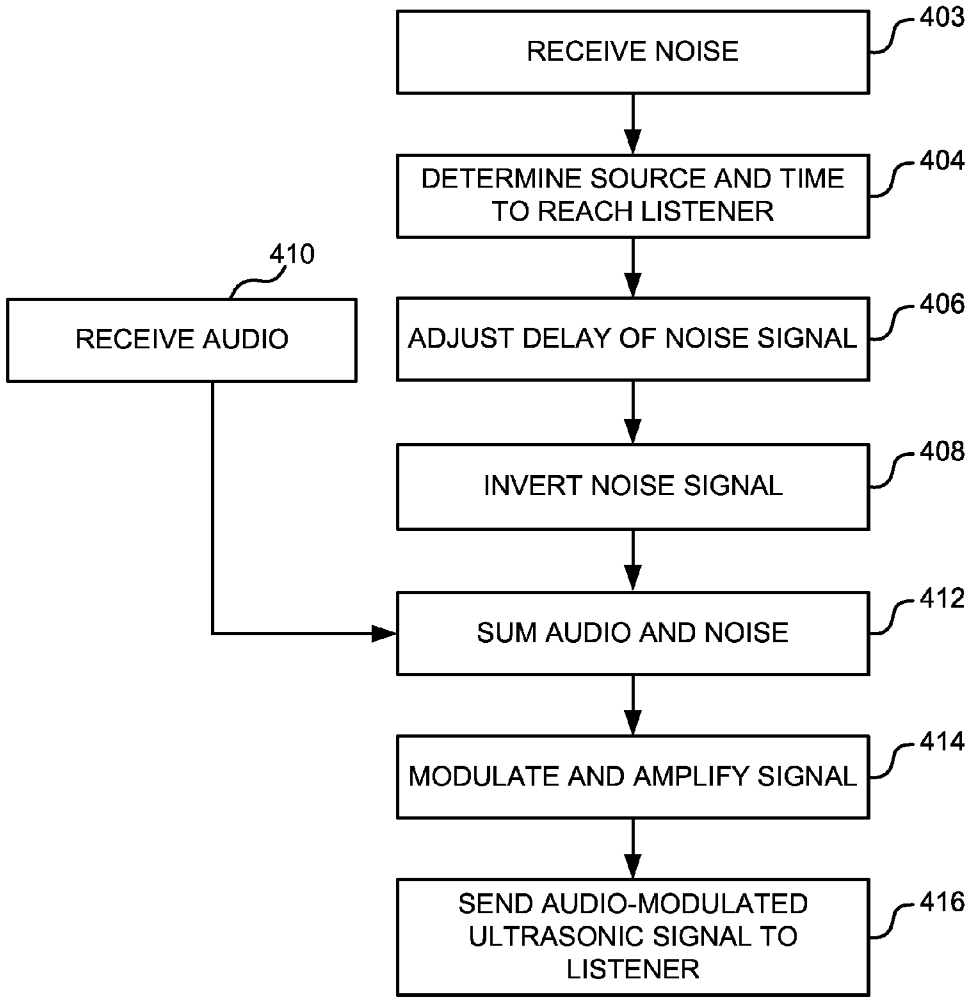
FIG. 5 is a diagram illustrating an example process for canceling noise in an environment in accordance with one embodiment of the technology described herein.

FIG. 5 is a diagram illustrating an example process for canceling noise in an environment in accordance with one embodiment of the technology described herein. Referring now to FIG. 5, at operation 403 the ultrasonic emitter system receives noise to be canceled. As noted above, in some embodiments, the noise can be received from a noise detection system such as noise detection module 205. The noise can be received over a wired or wireless connection. The received noise is typically an electronic signal representation of the noise such as that produced by a microphone and amplified by an amplifier. At operation 404, the ultrasonic emitter system determines the source of the noise and the time it will take for the noise to reach the listener. For example, various noise detection modules 205 can be configured to include an identification with the noise signals that they send to the ultrasonic emitter system. Identification codes placed in a packet header, or other like identification techniques, depending on the communications protocol, can be used to identify the source of the noise signal. In other embodiments, noise detection systems can be hardwired into various ports of the ultrasonic emitter system. Accordingly, in such embodiments, identification of the noise detection systems can be done based on the port by which the signal enters the system.

At operation 406, the ultrasonic emitter system can use a transfer function to adjust the amount of delay, equalization and reverb in the noise signal. The creation of such a transfer function is described in more detail below. In some embodiments, the delay can be provided by injecting delay into the system such as, for example, by buffering the information or bar running it through delay lines. As noted above, the amount of delay is calculated based on the relative distances of the components and the listener relative to one another. As noted, it is desirable to provide the appropriate amount of delay such that the inverted noise signal reaches a listener at the same time as the corresponding counterparts of the actual noise signal. Information pertaining to the locations of the components in the listener can be received by the system in real time for either a dynamic or a static environment or stored in the system a database or memory such as, for example, for a static system. For a static system, the amount of delay, dx, that should be injected into the system for a given noise detection system can also be stored so that this delay does not need to be calculated each time noise is received from that source.

At operation 408, the delayed noise signal can be inverted. As will be apparent to one of ordinary skill in the art after reading this description, the introduction of delay and the inversion of the signal can be performed in the opposite order. However, because the amount of delay may, in some embodiments, be dependent on the source of the noise signal, such embodiments will preferably not insert delay before determining which noise detection system delivered the noise signal to the emitter system.

As noted above, in some embodiments the noise cancelation system can be implemented in a system otherwise configured to deliver audio content to the listener. In such embodiments, at operations 410, the ultrasonic emitter system receives this audio content. Audio content can be received, for example, from sources such as audio source 2 in FIG. 1. The audio content can be equalized, compressed, and filtered, as appropriate for the content, by the ultrasonic emitter system.

At operation 412, the ultrasonic emitter system combines the audio content and the inverted noise signal into a combined signal. In some embodiments, this can be performed by summing the two audio components together. At operation 414, the sound audio signal is modulated onto an ultrasonic carrier and amplified for delivery to the user via an ultrasonic emitter. In the illustrated example, modulation onto an ultrasonic carrier is performed after the audio and inverted noise signals are combined. In other embodiments, modulation onto an ultrasonic carrier can be performed before the audio and inverted noise signals are combined.

At operation 416, an ultrasonic emitter launches the ultrasonic signal into the air sending the audio modulated ultrasonic signal to the listener.

FIG. 6 is a diagram illustrating another example of an audio processing system 210 that can be used in a noise canceling ultrasonic emitter system. Referring now to FIG. 6, this example audio processing system 210 includes an audio processing module 312, a communication module 314, a noise and delay calculation module 316, a summing module 318, a modulator 322, and an amplifier 320. In environments where the ultrasonic emitter system is configured to provide audio content to the listener audio processing module 312 can be included and active to receive the audio content and process it for ultrasonic delivery. Audio processing module 312 can be configured to receive audio input from sources such as, for example, sources 2 in FIG. 1. Audio processing module 312 can include audio processing components such as compression, equalization, and filtering to process the audio content for delivery.

Communication module 314 can be included to provide communications between audio processing system 210 and other components in the system. Communication module 314 can include wired and wireless interfaces conforming to any of a variety of protocols including standardized or proprietary protocols. Communication module 314 can be configured to communicate with, for example, noise detection devices operating as part of the overall noise cancelation system.

Noise and delay calculation module 316 can be included and configured to invert the noise signal and calculate and insert the appropriate amount of delay into the noise signal. As noted above, the amount of delay is computed so as to cause the inverted noise delivered by the ultrasonic carrier to reach the listener at the same time, substantially the same time, or approximately the same time as the corresponding actual noise reaches the listener. A summing module 318 can also be provided to sum the inverted noise signal with a signal representing the audio content to be delivered. Modulator 322 and amplifier 320 can be provided in accordance with various embodiments described herein for modulators and amplifiers.

In various embodiments disclosed herein, it is desirable that the inverted noise signal reach the listener so that it is 180° or substantially 180° out of phase with the actual noise reaching the listener. This allows the inverted noise signal to cancel the actual noise signal more effectively when they combine at the listener. As the phase difference changes from 180°, the effect of the cancelation diminishes. For example, at 135° or 225° (i.e., plus/minus 45° from 180°), the noise reduction will typically be no better than about 3 db. More generally, the remaining noise NR after cancelation is related to the phase difference by $N_R=2\sin(\theta/2)$, where θ is the deviation from 180° and the input noise is magnitude 1. Accordingly, 10° from 180° only yields about 8 dB noise cancelation at best and so on.

In various embodiments, many of the operations performed by audio processing system 210, and other audio processing systems described herein, can be performed in either the analog or the digital domain. For example, audio processing, noise signal inversion, delay injection, summing, and modulation can all be performed in the digital domain as well as in the analog domain. As would be apparent to one of ordinary skill in the art after reading this description, where some or all of these operations are performed in the digital domain, analog-to-digital and digital-to-analog converters would be included.

In embodiments where the noise detection microphone (e.g., microphone 202) is positioned proximal to the listener's ear, it may be desirable to include a filter for the microphone to filter out ultrasonic frequencies impinging on the microphone. Such frequencies can "swamp" the microphone and the noise detection system. Also, directional microphones pointing away from the ultrasonic emitter will be useful to help avoid overpowering the system with ultrasonic energy.

In some embodiments, the room or area in which the system is operating can be mapped to predict reflections from sounds from various sources. This mapping can be used to create the appropriate canceling effect by the Ultrasonic Emitter System. Room dimensions and surface material compositions can be stored in the database and then information used by the system to calculate reflections that would be generated by various known audio source is in the room. This information can also be determined in real time using feedback. With this information, the appropriate phase adjusted signals can be created to cancel out the noise resulting from reflections, or to enhance the sound resulting from reflections.

Furthermore, with the various embodiments disclosed herein, other processing, in addition to delay injection, can be included to enhance the noise cancelation. For example, equalization and reverb can also be added to enhance the cancelation effect. This is because the room or environment in which the system is located will affect the actual noise sound as well as a noise cancelation sound, and these effects are preferably measured so that the appropriate processing can be built into the system. This can be accomplished with either a passive or an active arrangement.

For a passive arrangement, the system can be set up with fixed placement and measurement of microphone locations so that their distances and locations during use are known. The transfer functions, which can include a combination of the delay, equalization and reverb, can be set up based on these locations, as long as there are no changes to the room that are significant enough to affect the cancelation. If the room changes significantly (e.g., enough to materially negatively impact the performance of the noise cancelation) or if the noise detection modules (e.g., noise detection modules 205) are moved (again, moved a distance sufficient to materially negatively impact the performance of the noise cancelation), new transfer functions may need to be calculated.

For an active arrangement, a microphone can be positioned near the intended listener to measure (whether periodically or continually) the effectiveness of the noise cancelation operation, and to provide feedback regarding this effectiveness to the noise cancelation module. The noise cancelation module can be configured to use this feedback to adapt to the environment by adjusting the transfer functions. While this may be more flexible than the passive arrangement (and adaptable in real time), it does require an additional microphone at the user for feedback purposes.

Whether an active or passive configuration, different transfer functions can be established for each noise detection module, as the characteristics of the environment can affect the noise differently, depending on its source and its path to the listener. An extra microphone (e.g., a feedback microphone) can also be included for setup purposes to assist with characterization of the environment for calculating the transfer function(s). This microphone can also be used for feedback purposes to allow the system to measure the effectiveness of the noise cancelation. In such embodiments, the system can be configured to receive noise signals (signals representing the noises picked up by the microphones) from the various noise detection modules and from the feedback microphone. The system may be configured to determine differences between the noise at the noise detection modules and the noise reaching the listener (e.g., at the feedback microphone) to characterize the environment. These differences can be taken into account when applying delay, equalization (including phase and amplitude, for example) and reverb to the noise signals so that the noise signal processed for inversion is a close a replica as possible to the actual noise reaching the listener. In this manner, the inverted noise reaching the listener from the cancelation system can more effectively cancel the actual noises reaching the listener.

In various embodiments, steps can be made to calibrate the system for the appropriate amount of delay. For example, known sequences can be generated at the various sound detection systems and communicated to run through the ultrasonic emitter system to determine the latency of the communications between the systems. As another example, time-stamped packets or sequences can be sent from one component to another (e.g. from the sound detection system to the ultrasonic emitter system, or vice versa) and the travel time measured based on the time-stamped packets. For example, the received time can be compared to the timestamp to determine the latency associated with the transfer. Likewise, a return or acknowledgement packets can be sent upon receipt back to the transmitting device so the transmitting device can determine the travel time between devices. These communications latencies can be combined with known internal latencies of the devices to calculate the amount of delay in the system. These delay calculations can be stored and reused during normal operations. Upon system reconfiguration or modification, the system can be recalibrated and nude delay calculations made.

One example provided above describes one user listening to audio program from a media device such as, for example, conventional audio from a television, radio, stereo, or otherwise, and his or her companion who would prefer not to hear the same audio content. There are numerous other examples of environments for applications in which would be desirable to provide a noise cancelation system to cancel out sounds in a listening environment. For example, a guest and hotel may wish to cancel out sounds that are generated by noisy patrons in the hallway. Accordingly, an ultrasonic noise cancelation system can be configured with a microphone positioned so as to pick up the noise occurring in the hallway. For example, the microphone can be aimed at the door of the hotel room. Sounds of the noisy guests in the hallway can be detected by the microphone and provided to the audio processing system where they can be inverted to create a cancelation signal to generate an inverted noise sound. The emitter of the ultrasonic noise cancelation system can be positioned to be aimed at the head of the bed in which the user is sleeping, or, more directly, at the head of the user. The ultrasonic noise cancelation system can be configured to inject the appropriate amount of delay into the inverted noise signal and modulate the inverted noise signal onto an ultrasonic carrier, which is launched by the emitter toward the users bed. With the appropriate delay calculations, the inverted noise sound reaches the user at the same time as the corresponding noise from the hallway reaches the user.

As another example, residences, office buildings, or other establishments located near airports or railroad crossings can employ an ultrasonic noise cancelation system to cancel or reduce the amount of noise created by the airport or railroad. Similarly, ultrasonic noise cancelation systems can be placed in factories, shops, manufacturing facilities or other like industrial environments. Consider the example of a factory in which there are a number of machines that make a large amount of undesirable noise. Also consider the example in which there are workers in another area of factory that are bothered by that noise. In such an environment, directional microphones can be positioned to pick up the noise generated by the machines and provided to the ultrasonic noise cancelation system. The ultrasonic noise cancelation system can be configured to create an inverse of the noise, provide an appropriate amount of delay, and deliver the inverted noise by the ultrasonic emitter (modulated onto an ultrasonic carrier) to the area in which the factory workers are located. The noise sound reaching the workers can be canceled by the inverted version of the noise sound delivered by the ultrasonic emitter. The ultrasonic system can also be used to deliver audio content to the factory workers along with the noise cancelation signals. For example, public address announcements, instructions, music, or other audio content can be combined with the inverted noise signal and delivered to the workers by the ultrasonic system.

As yet a further example, an ultrasonic noise cancelation system can be used in an automobile, plane, train, boat or other vehicle to cancel wind noise, engine noise, exhaust noise, road noise, or other noises in such a vehicle. In accordance with embodiments described above, microphones can be placed in the environment and oriented so as to pick up the noise generated by the noise source. The signal representing the noise can be delivered to the noise cancelation system, which can invert the noise and insert the appropriate amount of delay prior to delivering the inverted noise to the listener. Ultrasonic emitters can be placed at various locations throughout the cabin to be aimed at a listener or group of listeners.

Figure 7:
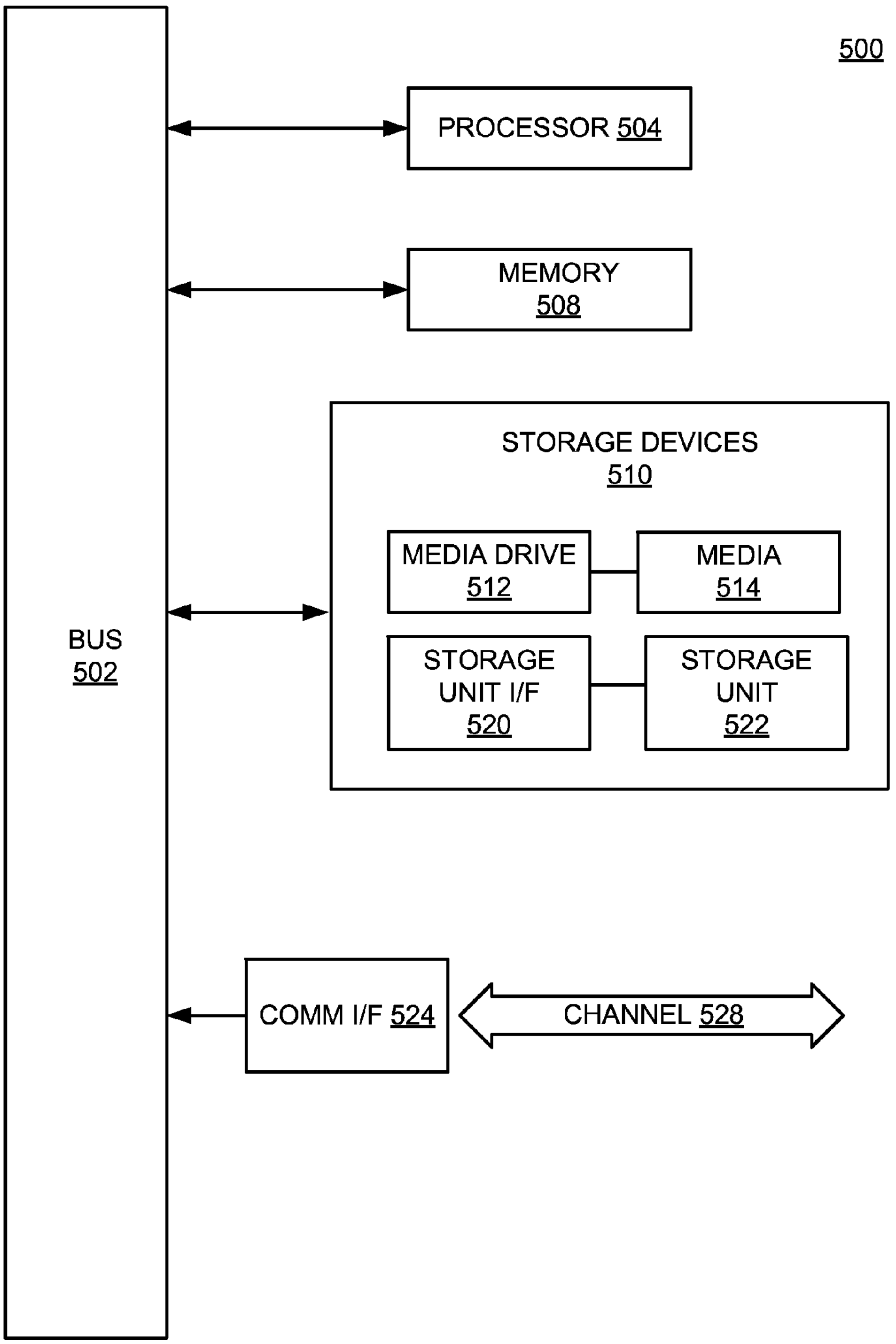
FIG. 7 illustrates an example computing module that may be used in implementing various features of embodiments of the disclosed technology.

As used herein, the term module might describe a given unit of functionality that can be performed in accordance with one or more embodiments of the technology disclosed herein. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the technology are implemented in whole or in part using software, in one embodiment, these software elements can be implemented to operate with a computing or processing module capable of carrying out the functionality described with respect thereto. One such example computing module is shown in FIG. 7. Various embodiments are described in terms of this example-computing module 500. After reading this description, it will become apparent to a person skilled in the relevant art how to implement the technology using other computing modules or architectures.

Referring now to FIG. 7, computing module 500 may represent, for example, computing or processing capabilities found within desktop, laptop and notebook computers; hand-held computing devices (PDA's, smart phones, cell phones, palmtops, etc.); mainframes, supercomputers, workstations or servers; or any other type of special-purpose or general-purpose computing devices as may be desirable or appropriate for a given application or environment. Computing module 500 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 500 might include, for example, one or more processors, controllers, control modules, or other processing devices, such as a processor 504. Processor 504 might be implemented using a general-purpose or special-purpose processing engine such as, for example, a microprocessor, controller, or other control logic. In the illustrated example, processor 504 is connected to a bus 502, although any communication medium can be used to facilitate interaction with other components of computing module 500 or to communicate externally.

Computing module 500 might also include one or more memory modules, simply referred to herein as main memory 508. For example, preferably random access memory (RAM) or other dynamic memory, might be used for storing information and instructions to be executed by processor 504. Main memory 508 might also be used for storing temporary variables or other intermediate information during execution of instructions to be executed by processor 504. Computing module 500 might likewise include a read only memory ("ROM") or other static storage device coupled to bus 502 for storing static information and instructions for processor 504.

The computing module 500 might also include one or more various forms of information storage mechanism 510, which might include, for example, a media drive 512 and a storage unit interface 520. The media drive 512 might include a drive or other mechanism to support fixed or removable storage media 514. For example, a hard disk drive, a floppy disk drive, a magnetic tape drive, an optical disk drive, a CD or DVD drive (R or RW), or other removable or fixed media drive might be provided. Accordingly, storage media 514 might include, for example, a hard disk, a floppy disk, magnetic tape, cartridge, optical disk, a CD or DVD, or other fixed or removable medium that is read by, written to or accessed by media drive 512. As these examples illustrate, the storage media 514 can include a computer usable storage medium having stored therein computer software or data.

In alternative embodiments, information storage mechanism 510 might include other similar instrumentalities for allowing computer programs or other instructions or data to be loaded into computing module 500. Such instrumentalities might include, for example, a fixed or removable storage unit 522 and an interface 520. Examples of such storage units 522 and interfaces 520 can include a program cartridge and cartridge interface, a removable memory (for example, a flash memory or other removable memory module) and memory slot, a PCMCIA slot and card, and other fixed or removable storage units 522 and interfaces 520 that allow software and data to be transferred from the storage unit 522 to computing module 500.

Computing module 500 might also include a communications interface 524. Communications interface 524 might be used to allow software and data to be transferred between computing module 500 and external devices. Examples of communications interface 524 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 524 might typically be carried on signals, which can be electronic, electromagnetic (which includes optical) or other signals capable of being exchanged by a given communications interface 524. These signals might be provided to communications interface 524 via a channel 528. This channel 528 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 508, storage unit 520, media 514, and channel 528. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 500 to perform features or functions of the disclosed technology as discussed herein.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. An ultrasonic audio system for canceling a noise sound from a listening environment, comprising:
- an audio processing system, comprising:
  - a communication module configured to receive a noise signal detected by a noise detection module, the noise signal representing the noise sound in a listener environment;
  - a noise cancelation module configured to invert the received noise signal thereby creating an inverse noise signal representing an inverse of the noise sound;
  - an equalization module configured to equalize the received noise signal either before or after it is inverted by the noise cancelation module; and
  - a modulator configured to modulate the equalized and inverse noise signal onto an ultrasonic carrier to generate an ultrasonic signal; and
- an ultrasonic emitter coupled to receive the ultrasonic signal and to launch an ultrasonic pressure wave representing the ultrasonic signal into a transmission medium in the listening environment toward an intended listener, wherein upon transmission in the transmission medium, the ultrasonic signal demodulates, thereby producing an inverse of the noise sound in the listening environment.

2. The ultrasonic audio system of claim 1, wherein the noise detection module comprises a microphone and a transmitter, wherein the microphone is configured to detect a noise sound and convert it to a noise signal representing the noise sound, and the transmitter is configured to transmit the noise signal to the audio processing system.

3. The ultrasonic audio system of claim 1, wherein the noise cancelation module is further configured to apply a transfer function to the noise signal, wherein the transfer function comprises applying at least one of a time delay and reverb to the noise signal either before or after it is inverted.

4. The ultrasonic audio system of claim 1, wherein the noise detection module is configured to be positioned proximal to the intended listener.

5. The ultrasonic audio system of claim 1, wherein the noise detection module is configured to be positioned remote from the intended listener's position.

6. The ultrasonic audio system of claim 1, wherein the audio processing system further comprises a delay calculation module configured to calculate an amount of time by which to delay the inverse noise signal such that when launched by the emitter, the inverse noise sound produced in the listening environment will reach an intended listener at substantially the same time as the noise sound reaches the intended listener.

7. The ultrasonic audio system of claim 6, wherein the audio processing system is further configured to delay the inverse noise signal by the calculated delay time.

8. The ultrasonic audio system of claim 6, wherein the amount of delay is calculated based on a first distance between the noise detection module and the intended listener and a second distance between the intended listener and the ultrasonic emitter.

9. The ultrasonic audio system of claim 8, further comprising a position determination module configured to determine a position of the intended listener in the listening environment and to use the determined position to determine the first and second distances.

10. The ultrasonic audio system of claim 1, wherein the audio processing system further comprises a reverberation module configured to apply reverb to the noise signal.

11. The ultrasonic audio system of claim 1, further comprising an audio processing module having an input to receive an audio content signal representing audio content for playback to the listener.

12. The ultrasonic audio system of claim 11, further comprising a summing module configured to combine the inverse noise signal with the audio content signal, and wherein the ultrasonic signal comprises the combined inverse noise signal and the audio content signal modulated onto the ultrasonic carrier.

13. The ultrasonic audio system of claim 1, further comprising the noise detection module, wherein the noise detection module comprises a microphone and a transmitter.

14. A method for canceling a noise sound from a listening environment utilizing ultrasonic, the method, comprising:
- an audio processing system receiving a noise signal detected by a noise detection module, the noise signal representing the noise sound in a listening environment;
- the audio processing system inverting the received noise signal thereby creating an inverse noise signal representing an inverse of the noise sound; and
- the audio processing system modulating the inverse noise signal onto an ultrasonic carrier to generate an ultrasonic signal;
- an ultrasonic emitter receiving the ultrasonic signal and launching an ultrasonic pressure wave representing the ultrasonic signal into a transmission medium in the listening environment toward an intended listener, wherein upon transmission in the transmission medium, the ultrasonic signal demodulates, thereby producing an inverse of the noise sound in the listening environment; and
- calculating an amount of time by which to delay the inverse noise signal such that when launched by the emitter, the inverse noise sound produced in the listening environment will reach the intended listener at substantially the same time as the noise sound reaches the intended listener, wherein the amount of delay is calculated based on a first distance between the noise detection module and the intended listener and a second distance between the intended listener and the ultrasonic emitter.

15. The method according to claim 14, further comprising delaying the inverse noise signal by the calculated delay time.

16. The method according to claim 14, further comprising determining a position of the intended listener in the listening environment and using the determined position to determine the first and second distances.

17. The method according to claim 14, further comprising receiving an audio content signal representing audio content for playback to the listener.

18. The method according to claim 17, further comprising combining the inverse noise signal with the audio content signal, and wherein the ultrasonic signal comprises the combined inverse noise signal and the audio content signal modulated onto the ultrasonic carrier.

19. An ultrasonic audio system for canceling a noise sound from a listening environment, comprising a non-transitory storage medium coupled to a processing module and comprising program instructions stored thereon, which, when executed by the processing module cause the ultrasonic audio system to perform the operations of:

receiving a noise signal detected by a noise detection module, the noise signal representing the noise sound in a listening environment;

the audio processing system inverting the received noise signal thereby creating an inverse noise signal representing an inverse of the noise sound;

modulating the inverse noise signal onto an ultrasonic carrier to generate an ultrasonic signal; and receiving the ultrasonic signal and launching an ultrasonic pressure wave representing the ultrasonic signal into a transmission medium in the listening environment toward an intended listener, wherein upon transmission in the transmission medium, the ultrasonic signal demodulates, thereby producing an inverse of the noise sound in the listening environment; and calculating an amount of time by which to delay the inverse noise signal such that when launched by the emitter, the inverse noise sound produced in the listening environment will reach the intended listener at substantially the same time as the noise sound reaches the intended listener, wherein the amount of delay is calculated based on a first distance between the noise detection module and the intended listener and a second distance between the intended listener and the ultrasonic emitter.

20. The ultrasonic audio system of claim 19, wherein the operations further comprise delaying the inverse noise signal by the calculated delay time.

21. The ultrasonic audio system of claim 19, wherein the operations further comprise determining a position of the intended listener in the listening environment and using the determined position to determine the first and second distances.

22. The ultrasonic audio system of claim 19, wherein the operations further comprise receiving an audio content signal representing audio content for playback to the intended listener.

23. The ultrasonic audio system of claim 22, wherein the operations further comprise combining the inverse noise signal with the audio content signal, and wherein the ultrasonic signal comprises the combined inverse noise signal and the audio content signal modulated onto the ultrasonic carrier.

24. An ultrasonic audio system for canceling a noise sound from a listening environment, comprising:

an audio processing system, comprising:

a communication module configured to receive a noise signal detected by a noise detection module, the noise signal representing the noise sound in a listener environment;

a noise cancelation module configured to invent the received noise signal thereby creating an inverse noise signal representing an inverse of the noise sound;

a reverberation module configured to apply reverb to the received noise signal either before or after it is inverted by the noise cancelation module; and a modulator configured to modulate the reverbed and inverse noise signal onto an ultrasonic carrier to generate an ultrasonic signal; and an ultrasonic emitter coupled to receive the ultrasonic signal and to launch an ultrasonic pressure wave representing the ultrasonic signal into a transmission medium in the listening environment toward an intended listener, wherein upon transmission in the transmission medium, the ultrasonic signal demodulates, thereby producing an inverse of the noise sound in the listening environment.

25. The ultrasonic audio system of claim 24, wherein the noise detection module comprises a microphone and a transmitter, wherein the microphone is configured to detect a noise sound and convert it to a noise signal representing the noise sound, and the transmitter is configured to transmit the noise signal to the audio processing system.

26. The ultrasonic audio system of claim 24, wherein the noise cancelation module is further configured to apply a transfer function to the noise signal, wherein the transfer function comprises applying at least one of a time delay and equalization to the noise signal either before or after it is inverted.

27. The ultrasonic audio system of claim 24, wherein the noise detection module is configured to be positioned proximal to the intended listener.

28. The ultrasonic audio system of claim 24, wherein the noise detection module is configured to be positioned remote from the intended listener's position.

29. The ultrasonic audio system of claim 24, wherein the audio processing system further comprises a delay calculation module configured to calculate an amount of time by which to delay the inverse noise signal such that when launched by the emitter, the inverse noise sound produced in the listening environment will reach the intended listener at substantially the same time as the noise sound reaches the intended listener.

30. The ultrasonic audio system of claim 29, wherein the audio processing system is further configured to delay the inverse noise signal by the calculated delay time.

31. The ultrasonic audio system of claim 29, wherein the amount of delay is calculated based on a first distance between the noise detection module and the intended listener and a second distance between the intended listener and the ultrasonic emitter.

32. The ultrasonic audio system of claim 31, further comprising a position determination module configured to determine a position of the intended listener in the listening environment and to use the determined position to determine the first and second distances.

33. The ultrasonic audio system of claim 24, wherein the audio processing system further comprises an equalization module configured to apply an equalization to the noise signal.

34. The ultrasonic audio system of claim 24, further comprising an audio processing module having an input to receive an audio content signal representing audio content for playback to the listener.

35. The ultrasonic audio system of claim 34, further comprising a summing module configured to combine the inverse noise signal with the audio content signal, and wherein the ultrasonic signal comprises the combined inverse noise signal and the audio content signal modulated onto the ultrasonic carrier.

36. The ultrasonic audio system of claim 24, further comprising the noise detection module, wherein the noise detection module comprises a microphone and a transmitter.

37. An ultrasonic audio system for canceling a noise sound from a listening environment, comprising:

an audio processing system, comprising:

a communication module configured to receive a noise signal detected by a noise detection module, the noise signal representing the noise sound in a listener environment;

a noise cancelation module configured to invert the received noise signal thereby creating an inverse noise signal representing an inverse of the noise sound; and a modulator configured to modulate the inverse noise signal onto an ultrasonic carrier to generate an ultrasonic signal;

an ultrasonic emitter coupled to receive the ultrasonic signal and to launch an ultrasonic pressure wave representing the ultrasonic signal into a transmission medium in the listening environment toward an intended listener, wherein upon transmission in the transmission medium, the ultrasonic signal demodulates, thereby producing an inverse of the noise sound in the listening environment; and a delay calculation module configured to calculate an amount of time by which to delay the inverse noise signal such that when launched by the emitter, the inverse noise sound produced in the listening environment will reach the intended listener at substantially the same time as the noise sound reaches the intended listener;

wherein the amount of delay is calculated based on a first distance between the noise detection module and the intended listener and a second distance between the intended listener and the ultrasonic emitter.

38. The ultrasonic audio system of claim 37, wherein the noise detection module comprises a microphone and a transmitter, wherein the microphone is configured to detect a noise sound and convert it to a noise signal representing the noise sound, and the transmitter is configured to transmit the noise signal to the audio processing system.

39. The ultrasonic audio system of claim 37, wherein the noise cancelation module is further configured to apply a transfer function to the noise signal, wherein the transfer function comprises applying at least one of a time delay, equalization, and reverb to the noise signal either before or after it is inverted.

40. The ultrasonic audio system of claim 37, wherein the noise detection module is configured to be positioned proximal to the intended listener.

41. The ultrasonic audio system of claim 37, wherein the noise detection module is configured to be positioned remote from the intended listener's position.

42. The ultrasonic audio system of claim 37, wherein the audio processing system further comprises and equalization module configured to apply an equalization to the noise signal.

43. The ultrasonic audio system of claim 37, wherein the audio processing system further comprises a reverberation module configured to apply reverb to the noise signal.

44. The ultrasonic audio system of claim 37, wherein the audio processing system is further configured to delay the inverse noise signal by the calculated delay time.

45. The ultrasonic audio system of claim 37, further comprising a position determination module configured to determine a position of the intended listener in the listening environment and to use the determined position to determine the first and second distances.

46. The ultrasonic audio system of claim 37, further comprising an audio processing module having an input to receive an audio content signal representing audio content for playback to the listener.

47. The ultrasonic audio system of claim 46, further comprising a summing module configured to combine the inverse noise signal with the audio content signal, and wherein the ultrasonic signal comprises the combined inverse noise signal and the audio content signal modulated onto the ultrasonic carrier.

48. The ultrasonic audio system of claim 37, further comprising the noise detection module, wherein the noise detection module comprises a microphone and a transmitter.

* * * * *